United States Patent
Krishnan et al.

(10) Patent No.: US 9,970,863 B2
(45) Date of Patent: May 15, 2018

(54) OPTICAL METROLOGY WITH REDUCED FOCUS ERROR SENSITIVITY

(71) Applicant: KLA-Tencor Corporation, Milpitas, CA (US)

(72) Inventors: Shankar Krishnan, Santa Clara, CA (US); Guorong V. Zhuang, San Jose, CA (US); David Y. Wang, Santa Clara, CA (US); Xuefeng Liu, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 148 days.

(21) Appl. No.: 14/833,370

(22) Filed: Aug. 24, 2015

(65) Prior Publication Data
US 2016/0245741 A1    Aug. 25, 2016

Related U.S. Application Data

(60) Provisional application No. 62/119,243, filed on Feb. 22, 2015.

(51) Int. Cl.
*G01N 21/25* (2006.01)
*G01J 3/02* (2006.01)
(Continued)

(52) U.S. Cl.
CPC .......... *G01N 21/255* (2013.01); *G01J 3/0205* (2013.01); *G01N 21/211* (2013.01);
(Continued)

(58) Field of Classification Search
CPC ..................................................... G01N 21/35
(Continued)

(56) References Cited

U.S. PATENT DOCUMENTS 5,333,052 A * 7/1994 Finarov .............. G01B 11/0641
                                                                    356/369
5,608,526 A    3/1997 Piwonka-Corle et al.
(Continued)

OTHER PUBLICATIONS

International Search Report and Written Opinion dated May 23, 2016, for PCT Application No. PCT/US2016/017399 filed on Feb. 10, 2016, by KLA-Tencor Corporation, 3 pages.

*Primary Examiner* — Tarifur Chowdhury
*Assistant Examiner* — Omar Nixon
(74) *Attorney, Agent, or Firm* — Spano Law Group; Joseph S. Spano

(57) ABSTRACT

Methods and systems for performing broadband spectroscopic metrology with reduced sensitivity to focus errors are presented herein. Significant reductions in sensitivity to focus position error are achieved by imaging the measurement spot onto the detector such that the direction aligned with the plane of incidence on the wafer surface is oriented perpendicular to the direction of wavelength dispersion on the detector surface. This reduction in focus error sensitivity enables reduced focus accuracy and repeatability requirements, faster focus times, and reduced sensitivity to wavelength errors without compromising measurement accuracy. In a further aspect, the dimension of illumination field projected on the wafer plane in the direction perpendicular to the plane of incidence is adjusted to optimize the resulting measurement accuracy and speed based on the nature of target under measurement.

20 Claims, 8 Drawing Sheets

(51) Int. Cl.
*G01N 21/95* (2006.01)
*G01N 21/21* (2006.01)
*G01N 21/55* (2014.01)

(52) U.S. Cl.
CPC ......... *G01N 21/55* (2013.01); *G01N 21/9501* (2013.01); *G01N 2021/213* (2013.01); *G01N 2201/068* (2013.01); *G01N 2201/06113* (2013.01)

(58) Field of Classification Search
USPC ........................................................ 356/300
See application file for complete search history.

(56) References Cited

U.S. PATENT DOCUMENTS

| | | | |
|---|---|---|---|
| 5,859,424 A | 1/1999 | Norton et al. | |
| 6,429,943 B1 | 8/2002 | Opsal et al. | |
| 6,590,656 B2 * | 7/2003 | Xu | G01B 11/0641 257/E21.53 |
| 6,633,831 B2 | 10/2003 | Nikoonahad et al. | |
| 6,734,967 B1 | 5/2004 | Piwonka-Corle et al. | |
| 6,816,570 B2 | 10/2004 | Janik et al. | |
| 6,829,049 B1 * | 12/2004 | Uhrich | G01N 21/211 356/369 |
| 6,895,075 B2 | 5/2005 | Yokhin et al. | |
| 6,972,852 B2 | 12/2005 | Opsal et al. | |
| 7,478,019 B2 | 1/2009 | Zangooie et al. | |
| 7,826,071 B2 | 11/2010 | Shchegrov et al. | |
| 7,929,667 B1 | 4/2011 | Zhuang et al. | |
| 7,933,026 B2 | 4/2011 | Opsal et al. | |
| 2002/0033945 A1 * | 3/2002 | Xu | G01B 11/0641 356/369 |
| 2003/0071996 A1 * | 4/2003 | Wang | G01B 11/00 356/369 |
| 2003/0076497 A1 * | 4/2003 | Wolf | G01B 11/0666 356/369 |
| 2003/0133102 A1 | 7/2003 | Opsal | |
| 2004/0207836 A1 | 10/2004 | Chibber et al. | |
| 2006/0197948 A1 | 9/2006 | Norton et al. | |
| 2009/0279090 A1 | 11/2009 | Wolf et al. | |
| 2010/0007863 A1 | 1/2010 | Jordanoska | |
| 2010/0296096 A1 * | 11/2010 | Horvath | G01B 11/0625 356/446 |
| 2012/0268744 A1 * | 10/2012 | Wolf | G01B 11/0625 356/447 |
| 2013/0114085 A1 * | 5/2013 | Wang | G01N 21/55 356/445 |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |

* cited by examiner

US 9,970,863 B2

OPTICAL METROLOGY WITH REDUCED FOCUS ERROR SENSITIVITY

CROSS REFERENCE TO RELATED APPLICATION

The present application for patent claims priority under 35 U.S.C. § 119 from U.S. provisional patent application Ser. No. 62/119,243, entitled "Apparatus and Methods of High Throughput Large NA Optical Metrology System," filed Feb. 22, 2015, the subject matter of which is incorporated herein by reference in its entirety.

TECHNICAL FIELD

The described embodiments relate to metrology systems and methods, and more particularly to methods and systems for improved measurement of semiconductor structures.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Ongoing reductions in feature size and increasing complexity of semiconductor devices impose difficult requirements on optical metrology systems. Optical metrology systems must meet high precision and accuracy requirements for increasingly small metrology targets at high throughput (i.e., short move, acquire, and measure (MAM) times) to remain cost effective. In this context, focusing errors have emerged as a critical, performance limiting issue in the design of optical metrology systems. More specifically, maintaining focus with sufficient accuracy, particularly during high throughput operation (i.e., short MAM times) has become a critical issue for optical metrology systems having high sensitivity to focusing errors.

FIG. 1 depicts an exemplary, prior art metrology system 10 having high sensitivity to focusing errors. Metrology system 10 includes an illumination source 25 that generates a beam of illumination light 14 incidence on a wafer 15. The beam of illumination light 14 passes through illumination pupil 11, illumination field stop 12, and illumination optics 13 as the beam propagates from the illumination source 25 to wafer 15. Beam 14 illuminates a portion of wafer 15 over a measurement spot 16. A beam of collected light 17 is collected from measurement spot 16 by collection optics 18. Collected light 17 passes through collection field stop 19, collection pupil 20, and spectrometer slit 21. The beam of collected light 17 is diffracted by diffraction grating 22 to spatially disperse the beam of collected light according to wavelength. The wavelength dispersed, collected light is incident on the surface of a two dimensional detector (e.g., charge coupled device (CCD) 23. The CCD detector 23 converts the collected light into electrical signals indicative of spectral intensity of the collected light. As depicted in FIG. 1, the collected beam of light 17 includes two distinct wavelengths. Diffraction grating 22 causes a spatial separation between the two different wavelengths of light projected onto the surface of detector 23. In this manner, light collected from measurement spot 16 having a particular wavelength is projected onto detector 23 over spot 24A and light collected from measurement spot 16 having another, different wavelength is projected onto detector 23 over spot 24B.

As depicted in FIG. 1, the Z-axis is oriented normal to the surface of wafer 15. The X and Y axes are coplanar with the surface of wafer 15, and thus perpendicular to the Z-axis. The chief ray 26 of the beam of illumination light 14 and the chief ray 27 of the beam of collected light 17 define a plane of incidence. The X-axis is aligned with the plane of incidence and the Y-axis is orthogonal to the plane of incidence. In this manner, the plane of incidence lies in the XZ plane. The beam of illumination light 14 is incident on the surface of wafer 15 at an angle of incidence, $\alpha$, with respect to the Z-axis and lies within the plane of incidence.

FIG. 2A depicts a top-view of wafer 15 including a depiction of measurement spot 16 illuminated by the beam of illumination light 14 of FIG. 1. In the embodiment depicted in FIG. 1, the cross-section of the beam of illumination light 14 is circular in shape (e.g., at illumination field stop 12). However, the geometric projection of circular beam 14 onto the surface of wafer 15 results in an measurement spot 16 having an elongated shape aligned with the plane of incidence as depicted in FIG. 2A. For a circular beam of illumination light, the measurement spot 16 projected on the surface of wafer 15 is elliptical in shape. In general, oblique illumination of a surface results in a projected illumination area that is elongated relative to the illumination cross section and the direction of elongation is aligned with the plane of incidence. Moreover, the magnitude of the elongation increases as the angle of incidence increases. More specifically, the beam shape is inversely proportional to the cosine of the angle of incidence in the direction of the plane of incidence. In the absence of diffraction and aberration effects, the projected illumination light remains undistorted in the direction perpendicular to the plane of illumination (e.g., Y-direction).

As depicted in FIG. 1, measurement spot 16 is projected onto the surface of detector 23 in a wavelength dispersive manner. Prior art metrology systems such as metrology system 10 are configured such that the projection of the elongated direction of measurement spot 16 is aligned with the direction of wavelength dispersion on the surface of detector 23. The X'-axis depicted in FIG. 1 is representative of the projection of the elongated direction of measurement spot 16 (i.e., the X-axis) onto detector 23. As depicted in FIG. 1, the X'-axis is aligned with the direction of wavelength dispersion on the surface of detector 23.

FIG. 2B depicts a normal view of the surface of detector 23. As depicted in FIG. 2B, the projection of the elongated direction of measurement spot 16 is aligned with the direction of wavelength dispersion on the surface of detector 23. By way of example, the elongated direction of spots 24A and 24B is aligned with the wavelength dispersion direction. The wavelength dependent images (e.g., spots 24A and 24B) on the surface of detector 23 are integrated in the direction perpendicular to the wavelength dispersion direction to obtain a spectrum, i.e., intensity as a function of wavelength along the wavelength dispersion axis. For a CCD detector, charge is integrated in the direction perpendicular to wavelength dispersion to arrive at the spectrum.

When the measurement spot is imaged onto the detector such that the direction aligned with the plane of incidence on the wafer surface is aligned with the direction of wavelength dispersion on the detector surface, the resulting point spread function (PSF) is strongly wavelength dependent. The resulting PSF is highly peaked because the image intensity varies greatly in the elongated direction for a given wavelength. To properly capture the highly peaked PSD the spectrometer must acquire spectral data at high resolution. This increases measurement time and reduces throughput.

In another example, the resulting PSF for a particular wavelength depends on the angle of incidence when the elongated image, and corresponding elongated intensity distribution, is aligned with the direction of spectral dispersion. The resulting PSF broadens or narrows depending on the angle of incidence.

In another example, the resulting PSF is highly sensitive to focus errors. As the measurement target on wafer moves in and out of focus, the detected image of the measurement spot on the wafer changes size and shifts location. In addition, the location of the measurement spot on the wafer shifts. As illustrated in FIG. 3, when wafer 15 is in focus, the beam of illumination light 14 illuminates the wafer at location A. The beam of collected light 17 is wavelength dispersed and imaged onto detector 23 over spots 24A and 24B as illustrated in FIG. 4. As the wafer 15 is moved upward in the z-direction and is defocused by an amount, ΔZ, that is greater than zero, the beam of illumination light 14 illuminates the wafer at location C. The beam of collected light 17' is wavelength dispersed and imaged onto detector 23 over spots 24A' and 24B'. The resulting images are larger as the wafer is moved away from the focal plane of the optical system and the center position of the images shifts in the direction aligned with the wavelength dispersion direction. This shift in the wavelength dispersion direction results in spectral measurement errors as the wavelength to pixel mapping changes. As the wafer 15 is moved downward in the z-direction and is defocused by an amount, ΔZ, that is less than zero, the beam of illumination light 14 illuminates the wafer at location B. The beam of collected light 17" is wavelength dispersed and imaged onto detector 23 over spots 24A" and 24B". Again, the resulting images are larger as the wafer is moved away from the focal plane of the optical system and the center position of the images shifts in the direction aligned with the wavelength dispersion direction.

The measurement spot movement on wafer 15 due to focus error, i.e. ΔZ≠0, results in image movement along the spectrometer dispersive axis as a function of wavelength. Since wavelength calibration is performed in the focal plane, i.e., Z=0, any image movement in the spectrometer dispersive direction induced by focus errors makes the measured spectrum very sensitive to deviations from the wavelength calibration.

In some examples, the emission spectrum of the broadband light source includes one or more characteristic atomic lines, e.g., a Xenon arc lamp. The atomic lines may be used to track and correct focus errors. In prior art metrology systems, focus tracking and correction are essential for achieving measurement accuracy, and tool to tool matching.

However, if the broadband light source is a high brightness Laser Driven Light Source (LDLS) the characteristic atomic lines are no longer available for tracking and correction of focus errors. Furthermore, the sensitivity to focus errors becomes exacerbated for large numeric aperture (NA) optical metrology systems.

In summary, sensitivity to focus errors and errors induced by oblique illumination present limitations on the performance of metrology systems, and large NA optical metrology systems, in particular.

SUMMARY

Methods and systems for performing broadband spectroscopic metrology with reduced sensitivity to focus errors are presented herein. Significant reductions in sensitivity to focus position error are achieved by imaging the measurement spot onto the detector such that the direction aligned with the plane of incidence on the wafer surface is oriented perpendicular to the direction of wavelength dispersion on the detector surface. This reduction in focus error sensitivity enables reduced focus accuracy and repeatability requirements, faster focus times, and reduced sensitivity to wavelength errors without compromising measurement accuracy. These benefits are particularly evident in large numerical aperture optical metrology systems.

In one aspect, a broadband spectroscopic metrology system is configured such that the measurement spot is imaged onto the detector such that the direction aligned with the plane of incidence on the wafer surface is oriented perpendicular to the direction of wavelength dispersion on the detector surface. In this arrangement, the sensitivity of the metrology system to focus errors is greatly reduced. With reduced sensitivity to focus errors, precise measurements are obtained with shorter MAM times, and thus, higher throughput.

In a further aspect, the dimension of illumination field projected on the wafer plane in the direction perpendicular to the plane of incidence is adjusted to optimize the resulting measurement accuracy and speed based on the nature of target under measurement. In some embodiments, the illumination field stop projected on the wafer plane in the direction perpendicular to the plane of incidence is adjusted to shape the PSF to achieve a flat-top profile that is less sensitive to wavelength for each measurement application. In addition, the spectral resolution is adjusted to achieve optimize the measurement accuracy and speed based on the flat-top profile.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for performing broadband spectroscopic metrology with reduced sensitivity to focus errors are presented herein. In some examples, a twenty times reduction in sensitivity to focus position is achieved by imaging the measurement spot onto the detector such that the direction aligned with the plane of incidence on the wafer surface is oriented perpendicular to the direction of wavelength dispersion on the detector surface. This reduction in focus error sensitivity enables reduced focus accuracy and repeatability requirements, faster focus times, and reduced sensitivity to wavelength errors without compromising measurement accuracy. These benefits are particularly evident in large numerical aperture optical metrology systems.

In one aspect, a broadband spectroscopic metrology system is configured such that the measurement spot is imaged onto the detector such that the direction aligned with the plane of incidence on the wafer surface is oriented perpendicular to the direction of wavelength dispersion on the detector surface. In this arrangement, the sensitivity of the metrology system to focus errors is greatly reduced. With reduced sensitivity to focus errors, precise measurements are obtained with shorter MAM times, and thus, higher throughput.

Figure 5:
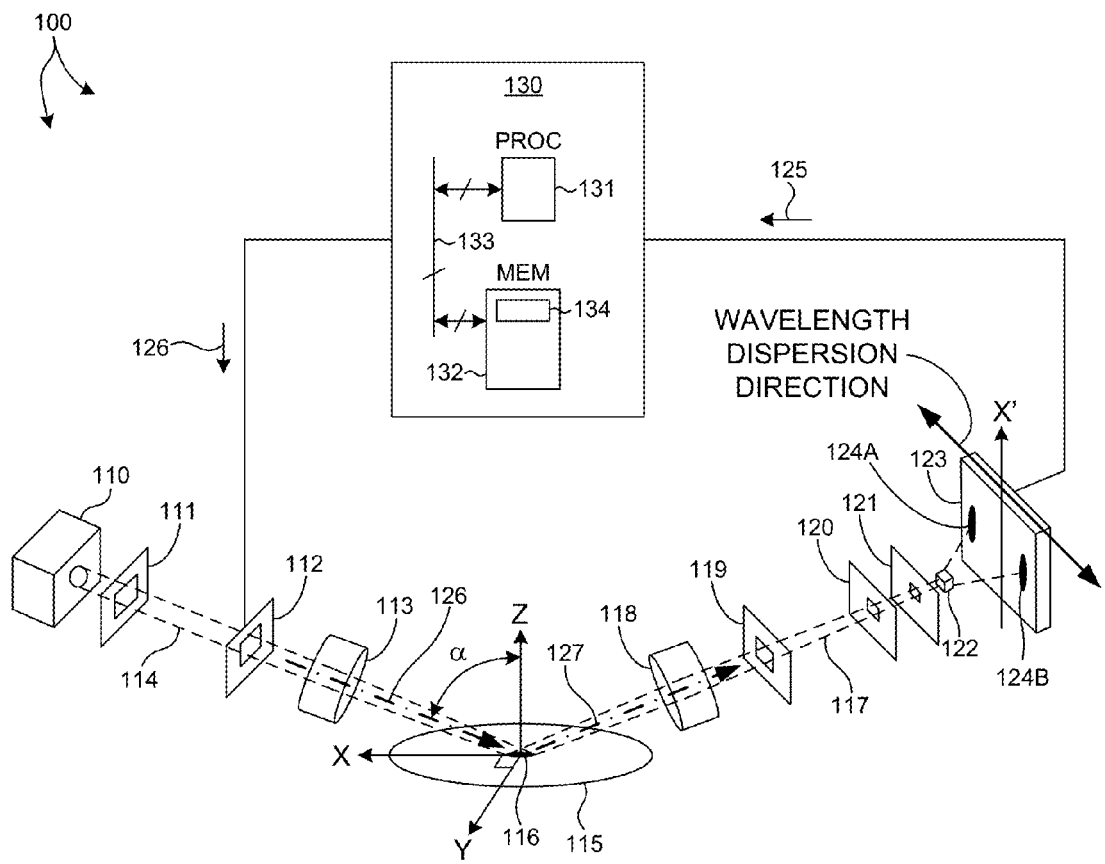
FIG. 5 depicts an exemplary, metrology system 100 having reduced sensitivity to focusing errors.

FIG. 5 depicts an exemplary, metrology system 100 having reduced sensitivity to focusing errors. Metrology system 100 may be configured as a broadband spectroscopic ellipsometer, reflectometer, or any combination thereof. Metrology system 100 includes an illumination source 110 that generates a beam of illumination light 114 incidence on a wafer 115. The beam of illumination light 114 passes through illumination pupil 111, illumination field stop 112, and illumination optics 113 as the beam propagates from the illumination source 110 to wafer 115. Beam 114 illuminates a portion of wafer 115 over a measurement spot 116. A beam of collected light 117 is collected from measurement spot 116 by collection optics 118. Collected light 117 passes through collection field stop 119, collection pupil 120, and spectrometer slit 121. The beam of collected light 117 is diffracted by diffraction grating 122 to spatially disperse the beam of collected light according to wavelength. The wavelength dispersed, collected light is incident on the surface of a two dimensional detector. In one example, detector 123 is a charge coupled device (CCD). However, in general, other two dimensional detector technologies may be contemplated (e.g., a position sensitive detector (PSD), an infrared detector, a photovoltaic detector, etc.). Detector 123 converts the collected light into electrical signals 125 indicative of spectral intensity of the collected light. As depicted in FIG. 5, the collected beam of light 117 includes two distinct wavelengths, by way of non-limiting example. Diffraction grating 122 causes a spatial separation between the two different wavelengths of light projected onto the surface of detector 123. In this manner, light collected from measurement spot 116 having a particular wavelength is projected onto detector 123 over spot 124A and light collected from measurement spot 116 having another, different wavelength is projected onto detector 123 over spot 124B.

As depicted in FIG. 5, the beam of illumination light 114 is provided to the surface of wafer 115 at an oblique angle. In general, illumination light may be provided to the surface of wafer 115 at any oblique angle or number of oblique angles. In some embodiments, an amount of illumination light is provided to the surface at normal incidence (i.e., aligned with the surface normal) in addition to oblique illumination.

In a further aspect, the amount of illumination light is broadband illumination light that includes a range of wavelengths spanning at least 500 nanometers. In one example, the broadband illumination light includes wavelengths below 250 nanometers and wavelengths above 750 nanometers. In general, the broadband illumination light includes wavelengths between 150 nanometers and 2,500 nanometers.

In some examples, the beam size of the amount of illumination light 114 projected onto the surface of wafer 115 is smaller than a size of a measurement target that is measured on the surface of the specimen. Exemplary beam shaping techniques are described in detail in U.S. Patent Application Publication No. 2013/0114085 by Wang et al., the contents of which are incorporated herein by reference in their entirety.

As depicted in FIG. 5, the Z-axis is oriented normal to the surface of wafer 115. The X and Y axes are coplanar with the surface of wafer 115, and thus perpendicular to the Z-axis. The chief ray 126 of the beam of illumination light 114 and the chief ray 127 of the beam of collected light 117 define a plane of incidence. The X-axis is aligned with the plane of incidence and the Y-axis is orthogonal to the plane of incidence. In this manner, the plane of incidence lies in the XZ plane. The beam of illumination light 114 is incident on the surface of wafer 115 at an angle of incidence, α, with respect to the Z-axis and lies within the plane of incidence.

Figure 1:
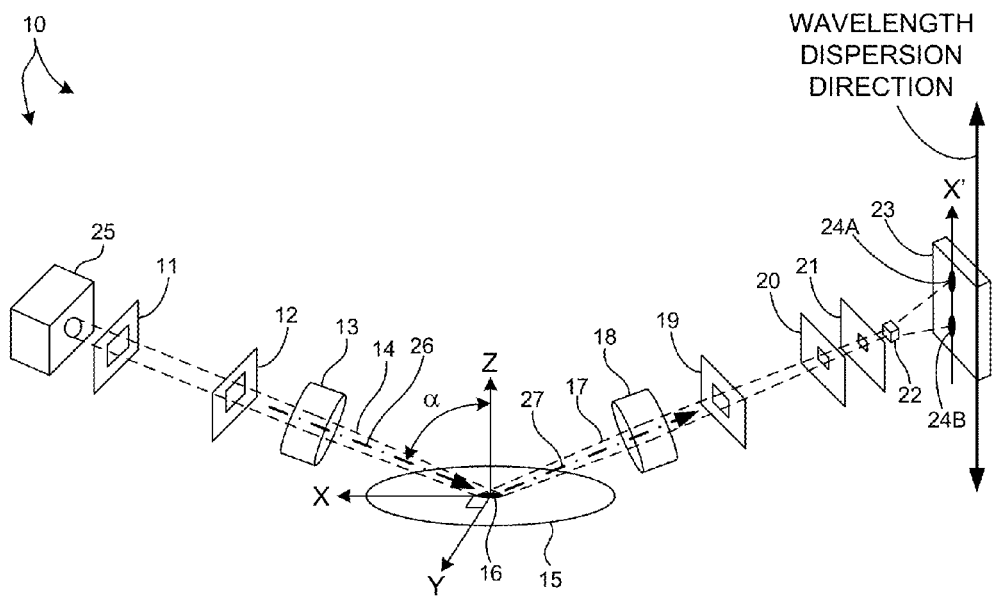
FIG. 1 depicts an exemplary, prior art metrology system 10 having high sensitivity to focusing errors.
Figure 2A:
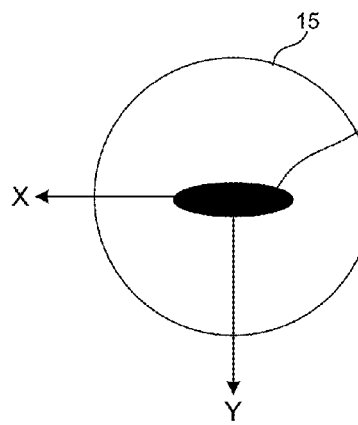
FIG. 2A depicts a top-view of wafer 15 including a depiction of measurement spot 16 illuminated by the beam of illumination light 14 of FIG. 1.
Figure 2B:
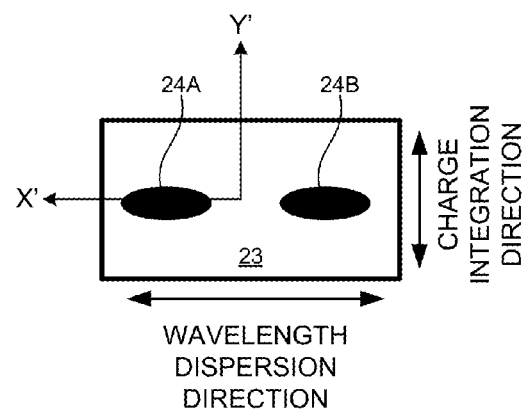
FIG. 2B depicts a normal view of the surface of detector 23 depicted in FIG. 1.

As described with respect to metrology system 10 depicted in FIG. 1, the geometric projection of a beam of illumination light onto the surface of a specimen at an oblique angle results in an elongation of the illumination beam cross-section in the direction aligned with the plane of incidence. By way of non-limiting example, a circular beam of illumination light projected on the wafer surface results in an illumination area that is elliptical in shape. Thus, in general, oblique illumination of a surface results in a projected illumination area that is elongated relative to the illumination cross section and the direction of elongation is aligned with the plane of incidence. Moreover, the magnitude of the elongation increases as the angle of incidence increases. More specifically, the beam shape is inversely proportional to the cosine of the angle of incidence in the direction of the plane of incidence. In the absence of diffraction and aberration effects, the projected illumination light remains undistorted in the direction perpendicular to the plane of illumination (e.g., Y-direction).

As depicted in FIG. 5, measurement spot 116 is projected onto the surface of detector 123 in a wavelength dispersive manner. Metrology system 100 is configured such that the projection of the elongated direction of measurement spot 116 is oriented perpendicular to the direction of wavelength dispersion on the surface of detector 123. The X'-axis depicted in FIG. 5 is representative of the projection of the elongated direction of measurement spot 116 (i.e., the X-axis) onto detector 123. As depicted in FIG. 5, the X'-axis is oriented perpendicular to the direction of wavelength dispersion on the surface of detector 123.

In the embodiment depicted in FIG. 5, all spectrometer components of metrology system 100 except the spectrometer slit are rotated ninety degrees with respect to the collected beam compared to metrology system 10 depicted in FIG. 1. In this manner, the projection of the elongated direction of measurement spot 116 is oriented perpendicular to the direction of wavelength dispersion.

Figure 12:
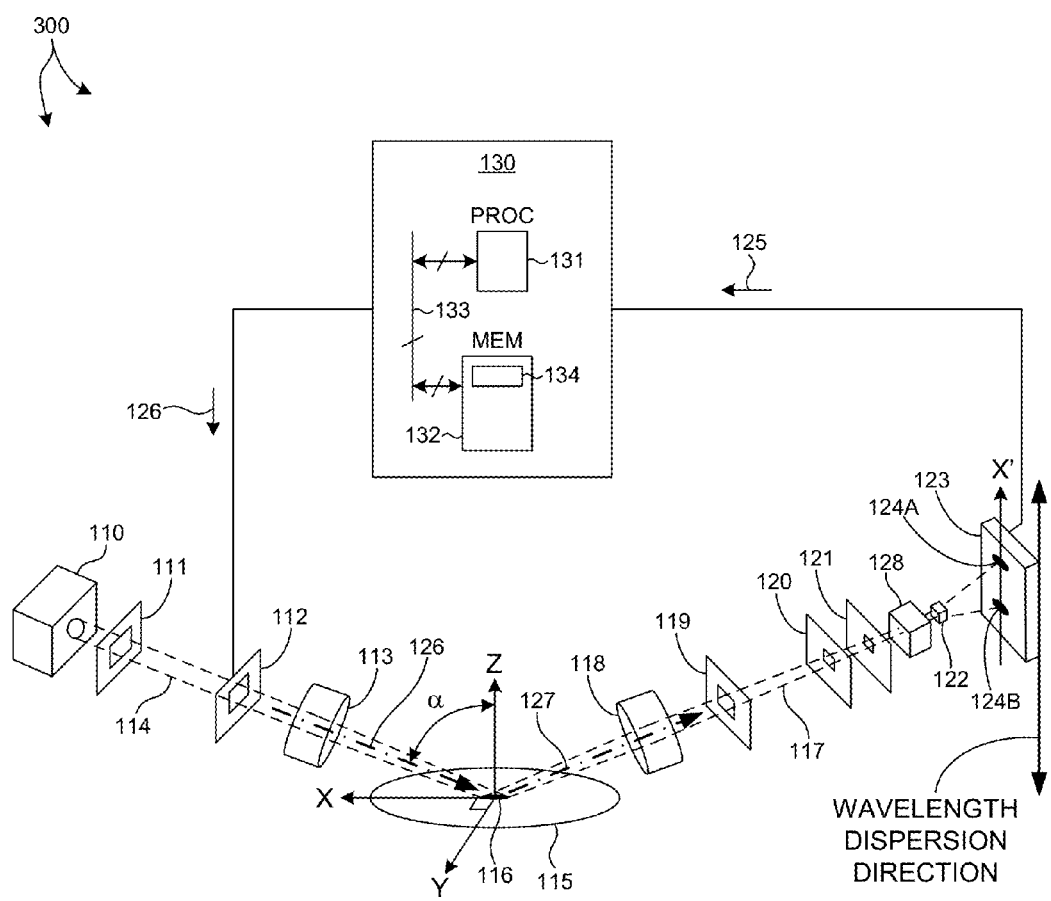
FIG. 12 depicts an exemplary, metrology system 300 having reduced sensitivity to focusing errors.

FIG. 12 depicts a metrology system 300 having reduced sensitivity to focus errors in another embodiment. Metrology system 300 includes like-numbered elements as described with reference to metrology system 100 depicted in FIG. 5. In addition, metrology system 300 includes beam rotation optics 128 placed in the collection path to rotate the image by ninety degrees (i.e., rotate the beam of collected light 117 along the beam axis). Metrology system 300 also differs from metrology system 100 in that all spectrometer components of metrology system 300 except the spectrometer slit (e.g., detector 123, grating 122, etc.) remain in the same orientation as metrology system 10 depicted in FIG. 1. The spectrometer slit of metrology system 300 is rotated ninety degrees with respect to the collected beam compared to metrology system 10 depicted in FIG. 1. In this manner, the projection of the elongated direction of measurement spot 116 is oriented perpendicular to the direction of wavelength dispersion.

Figure 6:
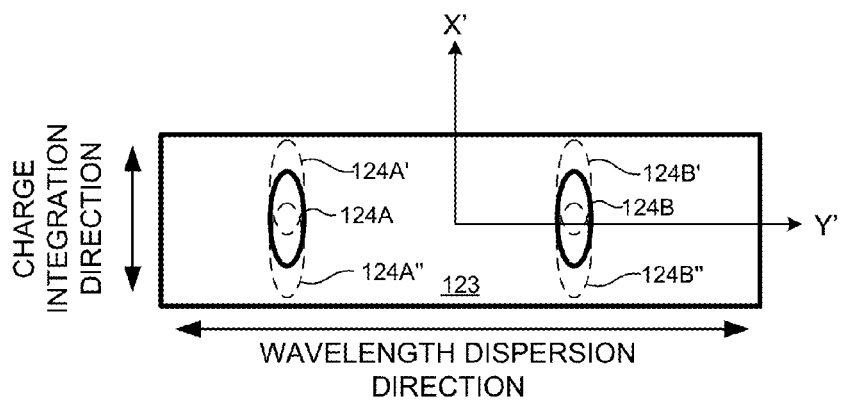
FIG. 6 depicts a normal view of the surface of detector 123 depicted in FIG. 5.

FIG. 6 depicts a normal view of the surface of detector 123. As depicted in FIG. 6, the projection of the elongated direction of measurement spot 116 (i.e., X'-axis) is oriented perpendicular to the direction of wavelength dispersion across the surface of detector 123. By way of example, the elongated direction of spots 124A and 124B is oriented perpendicular to the wavelength dispersion direction. The wavelength dependent images (e.g., spots 124A and 124B) on the surface of detector 123 are integrated in the direction perpendicular to the wavelength dispersion direction to obtain a spectrum, i.e., intensity as a function of wavelength along the wavelength dispersion axis. For a CCD detector, charge is integrated in the direction perpendicular to wavelength dispersion to arrive at the spectrum.

The images projected onto the surface of the detector (e.g., CCD 123) are integrated in the direction perpendicular to the spectrometer wavelength dispersive axis at each wavelength to obtain the measured spectrum. The individual spectral shape at each wavelength is the point spread function (PSF) of the system at that specific wavelength.

When the measurement spot is imaged onto the detector such that the direction aligned with the plane of incidence on the wafer surface is oriented perpendicular to the direction of wavelength dispersion on the detector surface, the resulting point spread function (PSF) is much less dependent on wavelength compared to prior art configurations. The resulting PSF is less peaked because the image intensity does not vary greatly in the direction perpendicular to the elongated direction (e.g., across the short axis of the ellipse) for a given wavelength. Furthermore, although the image intensity does vary greatly in the elongation direction (e.g., across the long axis of the ellipse), the variations are integrated out since the elongation direction is aligned with the charge integration direction of the CCD. In this manner, the spectrometer does not have to acquire spectral data at high resolution to accurately construct the PSF. This reduces measurement time and increases throughput.

In another example, the resulting PSF for a particular wavelength is independent of the angle of incidence when the elongation direction is oriented perpendicular to the direction of spectral dispersion. The image, and corresponding intensity distribution perpendicular to the elongation direction (i.e., across the short axis of the ellipse) is largely invariant to angle of incidence. Thus, the image, and corresponding intensity distribution, projected in the direction of spectral dispersion is largely invariant to angle of incidence. Hence, the calculated PSFs show little dependence on the angle of incidence.

Figure 3:
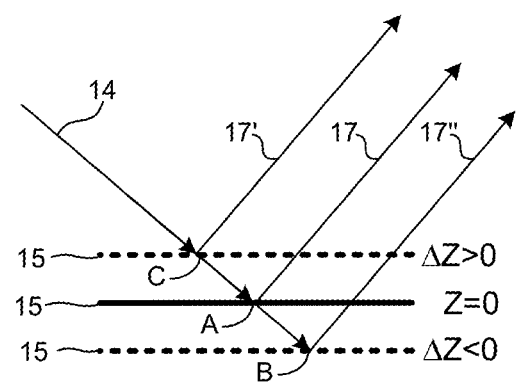
FIG. 3 illustrates a wafer 15 subject to focus position errors.
Figure 4:
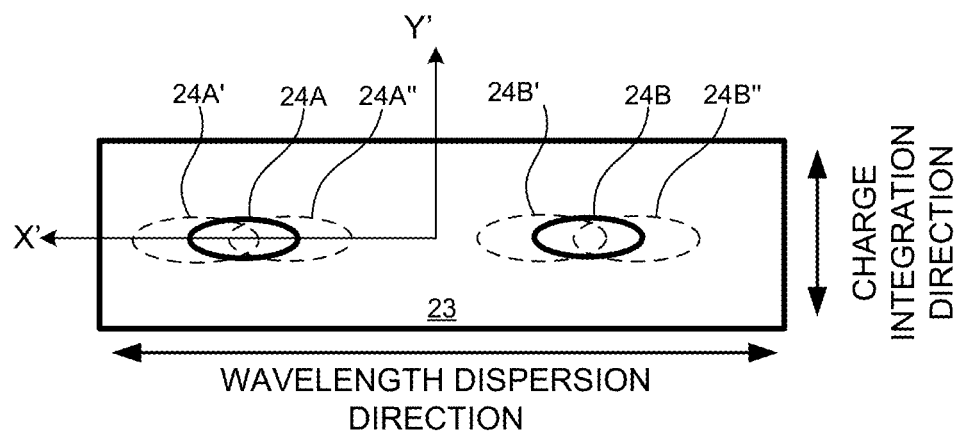
FIG. 4 illustrates a beam of collected light 17 that is wavelength dispersed and imaged onto the surface of detector 23.

In another example, the resulting PSF is significantly less sensitive to focus errors compared to prior art configurations. As the measurement target on wafer moves in and out of focus, the detected image of the measurement spot on the wafer shifts location. Analogous to the description of metrology system 10 and FIG. 3, when wafer 115 is in focus, the beam of illumination light 114 illuminates the wafer at location A. The beam of collected light 117 is wavelength dispersed and imaged onto detector 123 over spots 124A and 124B as illustrated in FIG. 6. As the wafer 115 is moved upward in the z-direction and is defocused by an amount, $\Delta Z$, that is greater than zero, the beam of illumination light 114 illuminates the wafer at location C. The beam of collected light 117' is wavelength dispersed and imaged onto detector 123 over spots 124A' and 124B'. This shift in image location perpendicular to the wavelength dispersion direction minimizes spectral measurement errors induced by focus errors as the wavelength to pixel mapping remains unchanged. As the wafer 115 is moved downward in the z-direction and is defocused by an amount, $\Delta Z$, that is less than zero, the beam of illumination light 114 illuminates the wafer at location B. The beam of collected light 117" is wavelength dispersed and imaged onto detector 123 over spots 124A" and 124B". Again, this shift in image location perpendicular to the wavelength dispersion direction minimizes spectral measurement errors induced by focus errors.

In this configuration, focus errors shift the image on the detector in the direction perpendicular to the wavelength dispersion axis. Since the calculated spectrum is obtained by integrating the image perpendicular to spectrometer dispersive axis, the focus error induced image shift is integrated out and does not induce substantial spectral measurement error. This reduced sensitivity to focus errors eliminates the need to track and correct focus errors based on atomic line emission. In this manner, broadband light sources such as a high brightness Laser Driven Light Source (LDLS) may be employed as a light source in spectroscopic metrology systems such as system 100 with relaxed focus positioning requirements.

As described hereinbefore, the PSF projected by the spectrometer is largely determined by the distribution of light perpendicular to the plane of incidence (i.e., XZ plane). For this reason, the PSF is independent of the oblique angle of incidence. Thus, the dependence of the PSF on wavelength is substantially less than a traditional configuration, such as the configuration described with reference to FIG. 1.

When the image in the AOI direction is perpendicular to the wavelength dispersion direction on the detector, as depicted in FIGS. 5-6, the PSF on the detector is limited by the geometric spot size in direction perpendicular to the plane of incidence.

In another further aspect, the dimension of illumination field stop projected on wafer plane in the direction perpendicular to the plane of incidence is adjusted to optimize the resulting measurement accuracy and speed based on the nature of target under measurement.

The illumination field stop projected on the wafer plane in the direction perpendicular to the plane of incidence is adjusted to shape the PSF to achieve a flat-top profile that is less sensitive to wavelength for each measurement application. In addition, the spectral resolution is adjusted to achieve optimize the measurement accuracy and speed based on the flat-top profile.

In some examples, e.g., if the sample is a very thick film or grating structure, the illumination field stop projected on wafer plane in the direction perpendicular to the plane of incidence is adjusted to reduce the field size to achieve increase spectral resolution. In some examples, e.g., if the sample is a thin film, the illumination field stop projected on wafer plane in the direction perpendicular to the plane of incidence is adjusted to increase the field size to achieve a shortened measurement time without losing spectral resolution.

Figure 7:
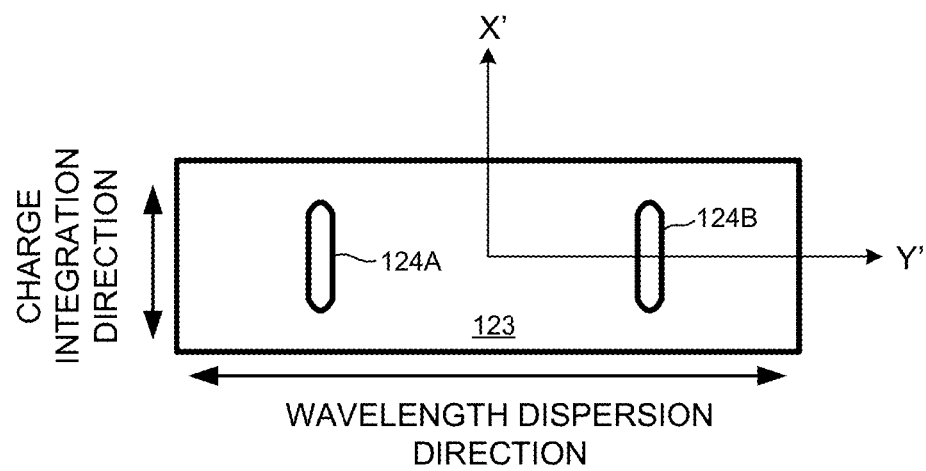
FIG. 7 depicts images 124A and 124B of measurement spot 116 projected onto detector 123.

FIG. 7 depicts spots 124A and 124B projected onto detector 123. In this example, the illumination field stop 112 depicted in FIG. 5 is adjusted to reduce the field size projected on the wafer plane in the direction perpendicular to the plane of incidence (i.e., the Y-direction). This, in turn, results in spots 124A and 124B projected onto detector 123 with reduced field size in the direction aligned with the wavelength dispersion direction.

In the embodiment depicted in FIG. 5, computing system 130 is configured to receive signals 125 indicative of the spectral response detected by CCD 123. Computing system 130 is further configured to determine control signals 126 that are communicated to programmable illumination field stop 112. Programmable illumination field stop 112 receives control signals 126 and adjusts the size of the illumination aperture to achieve the desired illumination field size.

In some examples, the illumination field stop is adjusted to optimize measurement accuracy and speed as described hereinbefore. In another example, the illumination field stop is adjusted to prevent image clipping by the spectrometer slit and corresponding degradation of measurement results. In this manner, the illumination field size is adjusted such that the image of the measurement target underfills the spectrometer slit. In one example, the illumination field stop is adjusted such that the projection of the polarizer slit of the illumination optics underfills the spectrometer slit of the metrology system.

Figure 8:
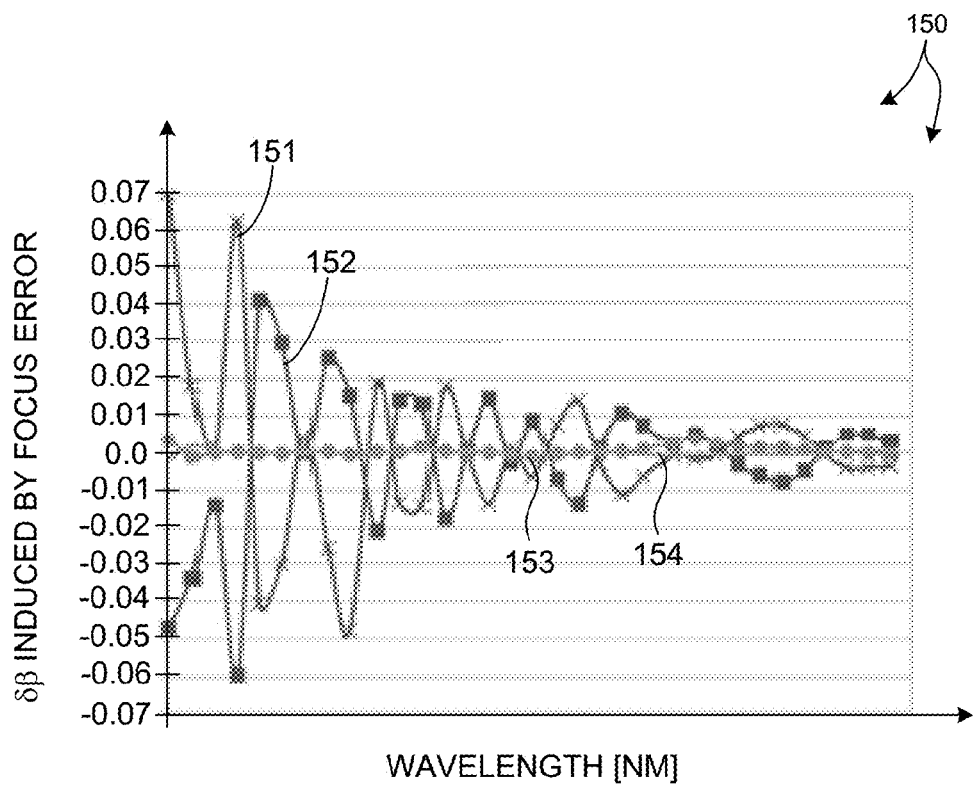
FIG. 8 depicts a plot 150 illustrative of simulation results indicating a reduced sensitivity to focus error for the system described with reference to FIG. 5 versus the system described with reference to FIG. 1.

When the measurement spot is imaged onto the detector such that the direction aligned with the plane of incidence on the wafer surface is oriented perpendicular to the direction of wavelength dispersion on the detector surface, the measurement results are much less sensitive to focus error. FIG. 8 depicts a plot 150 illustrative of simulation results indicating a reduced sensitivity to focus error for the system described with reference to FIG. 5 versus the system described with reference to FIG. 1. Plot 150 depicts the change in the spectrometer signal, $\beta$, induced by focus error for a number of different scenarios. The change in the spectrometer signal, $\delta\beta$, is the difference between the spectrometer signal measured when the target location is out of focus and the spectrometer signal measured when the target is located at nominal focus. Plotlines 151 and 152 indicate the values of $\delta\beta$ for a range of wavelengths that spans more than 500 nanometers with a +1 micrometer focus error and a −1 micrometer focus error, respectively, for a conventional metrology system such as that described with reference to FIG. 1. Plotlines 153 and 154 indicate the values of $\delta\beta$ for a range of wavelengths with a +1 micrometer focus error and a −1 micrometer focus error, respectively, for a novel metrology system such as that described with reference to FIG. 5. As illustrated in FIG. 8, the measurement results are much less sensitive to focus error when the measurement spot is imaged onto the detector such that the direction aligned with the plane of incidence on the wafer surface is oriented perpendicular to the direction of wavelength dispersion on the detector surface.

Figure 9:
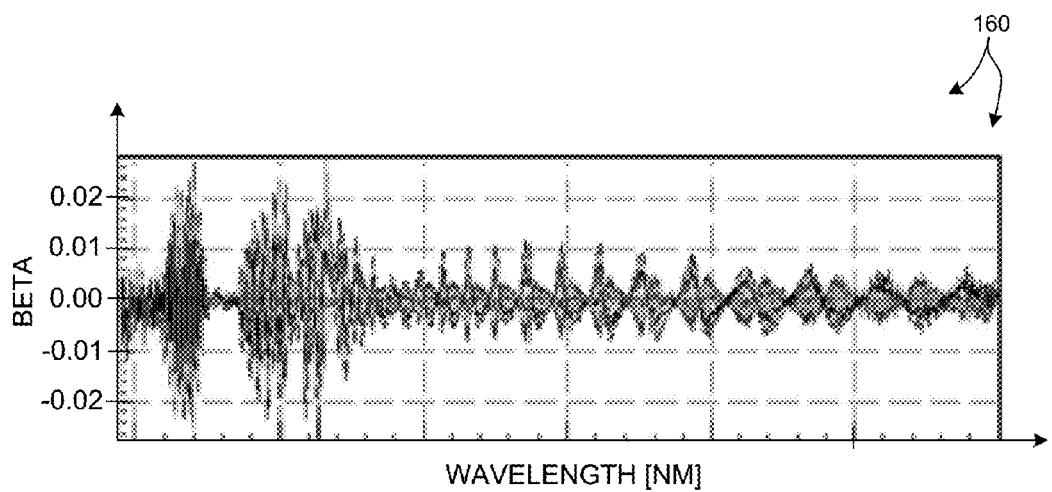
FIG. 9 depicts a plot 160 of values of the spectroscopic parameter, β, over a range of wavelengths for a series of thirty repeated measurements of a vertical NAND (VNAND) structure by a traditional broadband spectroscopic ellipsometer system such as the system described with reference to FIG. 1.

FIG. 9 depicts a plot 160 of values of the spectroscopic parameter, $\beta$, over a range of wavelengths that spans more than 500 nanometers for a series of thirty repeated measurements of a vertical NAND (VNAND) structure. The data depicted in FIG. 9 was generated by a traditional broadband spectroscopic ellipsometer system such as the system described with reference to FIG. 1.

Figure 10:
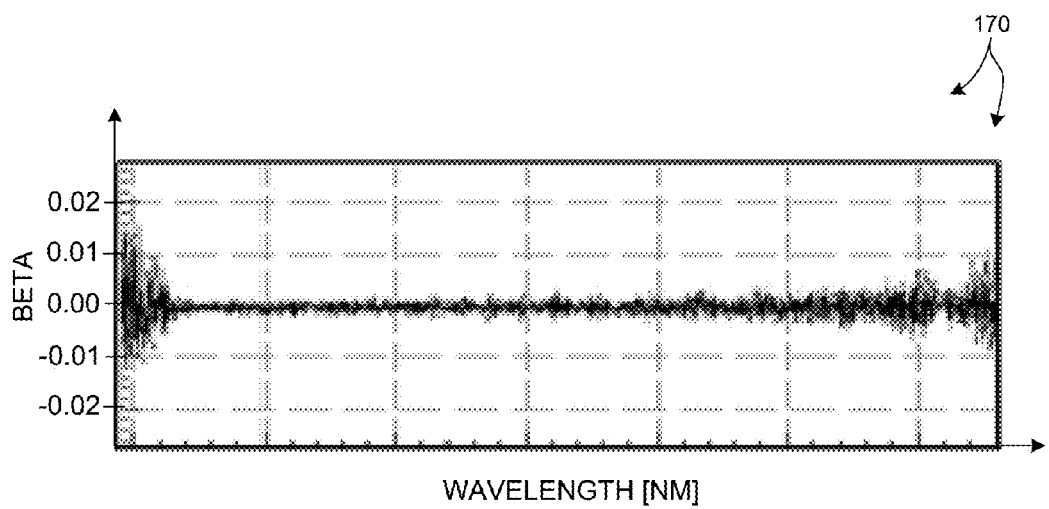
FIG. 10 depicts a plot 170 of values of the spectroscopic parameter, β, over a range of wavelengths for a series of thirty repeated measurements of the same vertical NAND (VNAND) structure by a broadband spectroscopic ellipsometer system that images the measurement spot onto the detector such that the direction aligned with the plane of incidence on the wafer surface is oriented perpendicular to the direction of wavelength dispersion on the detector surface.

FIG. 10 depicts a plot 170 of values of the spectroscopic parameter, $\beta$, over a range of wavelengths that spans more than 500 nanometers for a series of thirty repeated measurements of the same vertical NAND (VNAND) structure. The data depicted in FIG. 10 was generated by a broadband spectroscopic ellipsometer system that images the measurement spot onto the detector such that the direction aligned with the plane of incidence on the wafer surface is oriented perpendicular to the direction of wavelength dispersion on the detector surface. Such a system is described with reference to FIG. 5. Comparing the results of FIGS. 9 and 10, it is clear that imaging the measurement spot onto the detector such that the direction aligned with the plane of incidence on the wafer surface is oriented perpendicular to the direction of wavelength dispersion on the detector surface results in a significant improvement in system repeatability, primarily due to a reduced sensitivity to focus errors.

Figure 11:
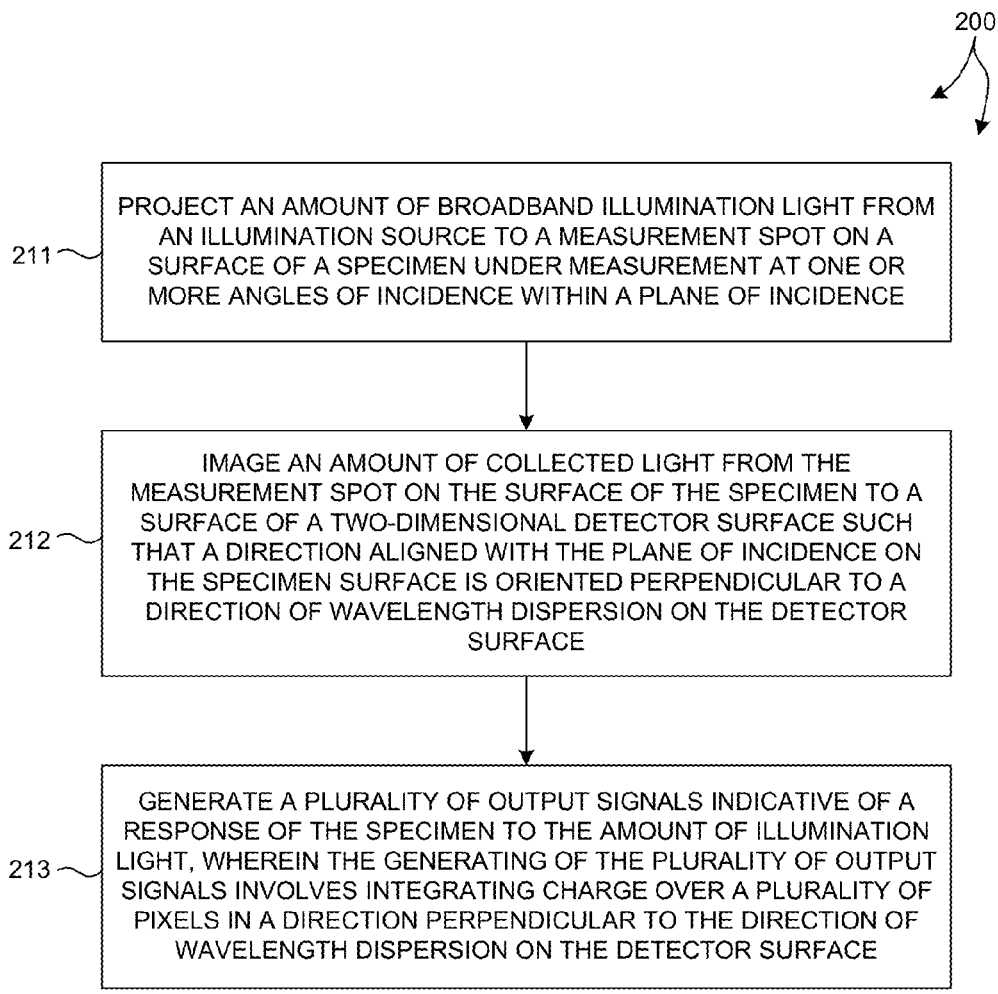
FIG. 11 illustrates a method 200 of performing spectroscopic measurements in at least one novel aspect as described herein.

FIG. 11 illustrates a method 200 of performing spectroscopic measurements in at least one novel aspect. Method 200 is suitable for implementation by a metrology system such as metrology system 100 illustrated in FIG. 5 of the present invention. In one aspect, it is recognized that data processing blocks of method 200 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 201, an amount of broadband illumination light from an illumination source is projected onto a measurement spot on a surface of a specimen under measurement at one or more angles of incidence within a plane of incidence.

In block 202, an amount of collected light from the measurement spot on the surface of the specimen is imaged to a surface of a two-dimensional detector surface such that a direction aligned with the plane of incidence on the specimen surface is oriented perpendicular to a direction of wavelength dispersion on the detector surface.

In block 203, a plurality of output signals indicative of a response of the specimen to the amount of illumination light is generated. The output signals are generated, at least in part, by integrating charge over a plurality of pixels in a direction perpendicular to the direction of wavelength dispersion on the detector surface.

In a further aspect, an estimate of a structural parameter of the specimen is determined based at least in part on the plurality of output signals.

As described herein any normal incidence or oblique incidence broadband optical metrology system may be configured such that the measurement spot is imaged onto the surface of the detector such that a direction aligned with the plane of incidence on the wafer surface is oriented perpendicular to a direction of wavelength dispersion on the detector surface. In some embodiments, the spectrometer dispersion axis is oriented orthogonal to wafer focus axis (e.g., z-axis in FIG. 5) to reduce the system sensitivity towards focus error.

Exemplary measurement techniques that may be configured as described herein include, but are not limited to spectroscopic ellipsometry (SE), including Mueller matrix ellipsometry, rotating polarizer SE, rotating polarizer, rotating compensator SE, rotating compensator, rotating compensator, SE, spectroscopic reflectometry (SR), including polarized SR, unpolarized SR, spectroscopic scatterometry, scatterometry overlay, beam profile reflectometry, both angle-resolved and polarization-resolved, beam profile ellipsometry, single or multiple discrete wavelength ellipsometry, x-ray relectivity (XRR), x-ray fluorescence (XRF), grazing incidence x-ray fluorescence (GIXRF), x-ray ellipsometry, etc. In general, any metrology technique that includes illumination having multiple wavelengths may be contemplated, individually, or in any combination. For example, any SR or SE technique applicable to the characterization of semiconductor structures, including image based metrology techniques, may be contemplated, individually, or in any combination.

In a further embodiment, system 100 includes one or more computing systems 130 employed to perform measurements of actual device structures based on spectroscopic measurement data collected in accordance with the methods described herein. The one or more computing systems 130 may be communicatively coupled to the spectrometer (e.g., spectrometer 123). In one aspect, the one or more computing systems 130 are configured to receive measurement data 125 associated with measurements of the structure of specimen 115.

It should be recognized that one or more steps described throughout the present disclosure may be carried out by a single computer system 130 or, alternatively, a multiple computer system 130. Moreover, different subsystems of the system 100, such as the spectroscopic ellipsometer 123, may include a computer system suitable for carrying out at least a portion of the steps described herein. Therefore, the aforementioned description should not be interpreted as a limitation on the present invention but merely an illustration.

In addition, the computer system 130 may be communicatively coupled to the spectrometer 123 in any manner known in the art. For example, the one or more computing systems 130 may be coupled to computing systems associated with the spectrometer 123. In another example, the spectrometer 123 may be controlled directly by a single computer system coupled to computer system 130.

The computer system 130 of the metrology system 100 may be configured to receive and/or acquire data or information from the subsystems of the system (e.g., spectrometer 123 and the like) by a transmission medium that may include wireline and/or wireless portions. In this manner, the transmission medium may serve as a data link between the computer system 130 and other subsystems of the system 100.

Computer system 130 of metrology system 100 may be configured to receive and/or acquire data or information (e.g., measurement results, modeling inputs, modeling results, reference measurement results, etc.) from other systems by a transmission medium that may include wireline and/or wireless portions. In this manner, the transmission medium may serve as a data link between the computer system 130 and other systems (e.g., memory on-board metrology system 100, external memory, or other external systems). For example, the computing system 130 may be configured to receive measurement data from a storage medium (i.e., memory 132 or an external memory) via a data link. For instance, spectral results obtained using spectrometer 123 may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a measurement model or an actual device parameter value determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 5, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some examples, the measurement models are implemented as an element of a SpectraShape® optical critical-dimension metrology system available from KLA-Tencor Corporation, Milpitas, Calif., USA. In this manner, the model is created and ready for use immediately after the spectra are collected by the system.

In some other examples, the measurement models are implemented off-line, for example, by a computing system implementing AcuShape® software available from KLA- Tencor Corporation, Milpitas, Calif., USA. The resulting, trained model may be incorporated as an element of an AcuShape® library that is accessible by a metrology system performing measurements.

In yet another aspect, the measurement model results described herein can be used to provide active feedback to a process tool (e.g., lithography tool, etch tool, deposition tool, etc.). For example, values of measured parameters determined based on measurement methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to a lithography tool, etch tool, or deposition tool.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:
1. A metrology system comprising:
an illumination source configured to generate an amount of illumination light;
an illumination optics subsystem configured to direct the amount of illumination light from the illumination source to a measurement spot on a surface of a speci- men under measurement at one or more angles of incidence within a plane of incidence;

a detector having a planar, two-dimensional surface sensitive to incident light, wherein the detector is configured to generate a plurality of output signals indicative of a response of the specimen to the amount of illumination light by integrating charge over a plurality of pixels in a direction perpendicular to a direction of wavelength dispersion on the detector surface; and a collection optics subsystem configured to collect an amount of collected light from the measurement spot on the surface of the specimen and direct the amount of collected light to the surface of the detector, wherein the collection optics subsystem images the measurement spot onto the surface of the detector such that a direction aligned with the plane of incidence on the wafer surface is oriented perpendicular to the direction of wavelength dispersion on the detector surface.

2. The metrology system of claim 1, wherein the amount of illumination light is broadband illumination light including a range of wavelengths spanning at least 500 nanometers.

3. The metrology system of claim 1, wherein at least a portion of the amount of illumination light is provided to the specimen at a normal angle of incidence.

4. The metrology system of claim 1, wherein at least a portion of the amount of illumination light is provided to the specimen at an oblique angle of incidence.

5. The metrology system of claim 1, wherein the metrology system is configured as any one or more of a spectroscopic ellipsometer and a spectroscopic reflectometer.

6. The metrology system of claim 1, wherein a projection of a polarizer slit of the illumination optics subsystem underfills a spectrometer slit of the metrology system.

7. The metrology system of claim 1, wherein the illumination source is a laser driven light source.

8. The metrology system of claim 1, wherein the illumination optics subsystem includes a programmable illumination field stop configured to limit an illumination field projected onto the specimen in a direction orthogonal to the plane of incidence.

9. The metrology system of claim 1, further comprising:
a controller configured to:
transmit a command signal to the programmable illumination field stop to alter a state of the illumination field stop to achieve a desired point spread function along the direction of wavelength dispersion on the detector surface.

10. The metrology system of claim 1, wherein a beam size of the amount of illumination light projected onto a surface of the specimen is smaller than a size of a measurement target that is measured on the surface of the specimen.

11. The metrology system of claim 1, wherein the detector is a charge coupled device (CCD) detector.

12. An apparatus comprising:
an illumination system configured to direct an amount of broadband illumination light from an illumination source to a measurement spot on a surface of a specimen under measurement at one or more angles of incidence within a plane of incidence;
a spectroscopic detector having a planar, two-dimensional surface sensitive to incident light, wherein the spectroscopic detector is configured to generate a plurality of output signals by integrating charge over a plurality of pixels in a direction perpendicular to a direction of wavelength dispersion on the detector surface; and
a collection optics subsystem configured to collect an amount of collected light from the measurement spot on the surface of the specimen and direct the amount of collected light to the surface of the spectroscopic detector, wherein the collection optics subsystem images the measurement spot onto the surface of the spectroscopic detector such that a direction aligned with the plane of incidence on the wafer surface is oriented perpendicular to the direction of wavelength dispersion on the spectroscopic detector surface.

13. The apparatus of claim 12, wherein the illumination system includes a programmable illumination field stop configured to limit an illumination field projected onto the specimen in a direction orthogonal to the plane of incidence.

14. The apparatus of claim 13, further comprising:
a controller configured to:
transmit a command signal to the programmable illumination field stop to alter a state of the illumination field stop to achieve a desired point spread function along the direction of wavelength dispersion on the detector surface.

15. A method comprising:
projecting an amount of broadband illumination light from an illumination source to a measurement spot on a surface of a specimen under measurement at one or more angles of incidence within a plane of incidence;
imaging an amount of collected light from the measurement spot on the surface of the specimen to a surface of a two-dimensional detector surface such that a direction aligned with the plane of incidence on the specimen surface is oriented perpendicular to a direction of wavelength dispersion on the detector surface; and
generating a plurality of output signals indicative of a response of the specimen to the amount of illumination light, wherein the generating of the plurality of output signals involves integrating charge over a plurality of pixels in a direction perpendicular to the direction of wavelength dispersion on the detector surface.

16. The method of claim 15, further comprising:
determining an estimate of a structural parameter based at least in part on the plurality of output signals.

17. The method of claim 15, wherein the amount of broadband illumination light includes a range of wavelengths spanning at least 500 nanometers.

18. The method of claim 15, wherein at least one of the one or more angles of incidence is an oblique angle of incidence.

19. The method of claim 15, further comprising:
limiting an extent of an illumination field projected onto the surface of the specimen in a direction orthogonal to the plane of incidence.

20. The method of claim 19, wherein the limiting of the extent of the illumination field involves transmitting a command signal to a programmable illumination field stop to alter a state of the illumination field stop to achieve a desired point spread function along the direction of wavelength dispersion on the detector surface.

* * * * *